US008419661B2

(12) United States Patent
Schweighofer et al.

(10) Patent No.: US 8,419,661 B2
(45) Date of Patent: Apr. 16, 2013

(54) UPPER LIMB MEASUREMENT AND REHABILITATION METHOD AND SYSTEM

(75) Inventors: Nicolas Schweighofer, Santa Monica, CA (US); Younggeun Choi, Los Angeles, CA (US); Cheol Han, Sungnam (KR); James Gordon, Arcadia, CA (US); Carolee J. Winstein, Los Angeles, CA (US); Rieko Osu, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/619,534

(22) Filed: Nov. 16, 2009

(65) Prior Publication Data

US 2010/0179453 A1    Jul. 15, 2010

Related U.S. Application Data

(60) Provisional application No. 61/114,929, filed on Nov. 14, 2008.

(51) Int. Cl.
*A61B 5/103* (2006.01)
*A61B 5/117* (2006.01)

(52) U.S. Cl.
USPC ........... 600/595; 600/558; 600/587; 273/440; 273/441; 273/445

(58) Field of Classification Search ................. 600/587, 600/595; 73/379.02, 379.09; 273/440, 441, 273/445
See application file for complete search history.

(56) References Cited

U.S. PATENT DOCUMENTS

| 5,490,517 | A  | * | 2/1996  | Whitman et al. ............. 600/587 |
| 2005/0065452 | A1 | * | 3/2005  | Thompson .................... 600/558 |
| 2006/0195018 | A1 | * | 8/2006  | Guillen ......................... 600/300 |
| 2007/0191141 | A1 | * | 8/2007  | Weber .......................... 473/446 |
| 2008/0288020 | A1 | * | 11/2008 | Einav et al. ..................... 607/48 |
| 2009/0129205 | A1 | * | 5/2009  | Reichow et al. ................. 368/9 |

OTHER PUBLICATIONS

Ronnqvist et al. (Article titled "Quantitative Assessment of Right and Left Reaching Movements in Infants: A Longitudinal Study from 6 to 36 Months"), Dev Psychobiol 48: 444-459, 2006.*
Mindy Lipson Aisen, et al., "*The Effect of Robot-Assisted Therapy and Rehabilitative Training on Motor Recovery Following Stroke*", Arch. Neurol, (1997): vol. 54, pp. 443-446.
J. Doyon, et al. "*Role of the Striatum, Cerebellum, and Frontal Lobes in the Learning of a Visuomotor Sequence*", Brain and Cognition, (1997): vol. 34, pp. 218-245.
H.I. Krebs, et al., "*Overview of clinical trials with MIT-MANUS: a robot-aided neuron-rehabilitation facility*", Technology and Health Care (1999): vol. 7, pp. 419-423.

(Continued)

*Primary Examiner* — Rene Towa
(74) *Attorney, Agent, or Firm* — DLA Piper LLP (US)

(57) ABSTRACT

A method for measuring an upper limb reaching capability of a user with an impaired limb is provided. Each upper limb is placed at a default position on a horizontal surface. A target is displayed from among a plurality of targets on the horizontal surface. One of the limbs reaches for the target. Limb choice, position information and elapsed time are sensed and recorded. The reaching limb is retracted to the default position. The displaying step through the retracting step are repeated for each of the plurality of targets, wherein each of the plurality of targets is spaced apart.

7 Claims, 6 Drawing Sheets

OTHER PUBLICATIONS

Randolph J. Nudo, "*Neural Substrates for the Effects of Rehabilitative Training on Motor Recovery After Ischemic Infarct*", Science, (1996): vol. 272, pp. 1791-1794.

Erik J. Plautz, et al., "*Role of Adaptive Plasticity in Recovery of Function After Damage to Motor Cortex*", Muscle & Nerve (2001): vol. 24, pp. 1000-1019.

* cited by examiner

Door Bell      Door Knob      Jar

FIG. 8

UPPER LIMB MEASUREMENT AND REHABILITATION METHOD AND SYSTEM

BACKGROUND OF THE INVENTION

1. Field of the Invention

This invention pertains to the field of rehabilitation patients with stroke. More particularly, the invention relates to methods and systems for rehabilitation patients with stroke.

2. Description of Related Art

Stroke is the leading cause of disability among American adults. Each year in the U.S., approximately 750,000 people suffer strokes and of those, nearly 400,000 survive with some level of neurological impairment and disability. Nearly three million people are affected by stroke-related disability, and the estimated financial burden is thirty billion dollars annually.

After stroke-hemiparesis or other brain lesions, one of the most important patient-centered goals is voluntary use of the paretic arm in daily life. Statistics indicate that over 80% of first-time strokes (infarctions only) involve acute hemiparesis of the upper limb that significantly affects the functional independence and health of the stroke survivor. Of all impairments that result from stroke, traditional rehabilitation methods are the least effective in treating hemiparesis of the upper limb. In addition, stroke often leaves individuals unable to perform functional movements with the impaired limb even though the limb is not completely paralyzed. Post-stroke individuals with relatively high upper extremity motor function often choose to perform daily activities with the less affected arm. In this regard, non-use has been defined as the difference between what a patient can do when forced to use a paretic arm and what the patient does when given a free choice to use either arm. This learned non-use, is most obvious during the early post-injury period but can improve with rehabilitation therapy (Nudo et al, 2001; Taub et al, 2003; Winstein et al, 2003). Limb choice is an important anticipatory pre-movement parameter that has received little attention from the neuro-rehabilitation research community.

Traditional methods of measuring use include the Motor Activity Log (MAL) and the Actual Amount of Use Test (AAUT). Such methods to measure non-use are not often practical, or even reproducible, given the nature of the tests. In the MAL, a participant is asked to rate the amount of use (AOU) and quality of movement (QOM) for the paretic arm over a specified period for each item. The MAL suffers from numerous drawbacks: 1) it relies on the participant's memory; 2) it takes at least one hour for a trained interviewer to conduct and score; 3) participants with discordant stroke may choose to not perform certain activities with the paretic hand simply because it is their non-dominant hand, thereby affecting the sensitivity of the MAL. In the AAUT, participants are asked to perform functional tasks while their performances are videotaped without the participants being aware of it. However, since the participants must be unaware of the videotaping, the test is time-consuming and difficult to administer repeatedly. Because we do not have good quick tests at present, therapists cannot accurately quantify progress of patient in normal clinic and cannot design effective individualized therapy. Other tests measure arm and hand function and impairments (e.g. Fugl-Meyer and WMFT), but are also lengthy and are not practical to administer given the often limited contact time between physical therapists and patients.

Recent clinical studies have found that intensive motor training can improve functional upper limb performance in patients. In particular, there is evidence that intensive task practice, in which patients actively engage in repeated attempts to produce motor behaviors beyond their present capabilities, is effective for improving upper extremity function after stroke (Butefisch, 1995; Kwakkel, 1999; Wolf, 2002). These data suggest that the potential for functional recovery after stroke lasts much longer than previously believed, and that the degree of recovery depends not only on the level of initial impairment but also on the amount, type, and intensity of task practice available to the patient during the recovery process.

In previous studies that demonstrated functional improvements after brain lesion and/or experience-dependent neuroplasticity show that a large amount of practice is needed to show improvement. In one experiment with monkeys, 9,600 pellet retrievals were carried out over 4 weeks (Nudo et al., 1996). In experiments with cats, 7,000 trials of a food catch task over 35 days were performed (Pavlides et al., 1993). In human studies, Doyou et al. (Doyon et al., 1997) trained their subjects for 2,400 repetitions of a 10 item sequence over 6 weeks, and Kami (Karni, 1995) reports 31,500 repetitions of a finger sequence task over 35 days.

The number of repetitions demonstrated by these studies is in dramatic contrast with the limited time spent by the typical stroke patient undergoing neurological rehabilitation in actual therapeutic activity. Lincoln and colleagues report that only 36 min per day is spent in contact with either a physical or an occupational therapist, and "in all settings [we] observed patients spent many hours doing nothing" (Lincoln et al., 1996). Further, (Mackey et al.; 1996) reports that patients spent 70% of the day in activities largely unrelated to a physical outcome and less than 20% of the day in activities that could potentially contribute to their recovery. Finally (Keith and Cowell, 1987) point out that patients spent 8.1% (39 minutes) of the day in physical therapy (but with an undetermined proportion of that doing practice).

Another problem with conventional medical rehabilitation models is that they are largely constrained by economic considerations (i.e., how many sessions the patient's health insurance will cover) and are therefore not adequate to maximize functional outcomes. Further, due to the belief that therapy is only marginally effective, health insurance companies often reject requests for rehabilitation past 3 months post stroke.

In view of the shortcomings of the conventional medical practice model, there is a growing interest in employing robotic technology for rehabilitation of upper extremity movements. The use of robotic systems for limb rehabilitation are known, but are provided such that the robot directly assists the movements of an impaired limb. Current robots do not retrain functional tasks such as those requiring tool and object reaching and manipulation with grasping. Instead, they retrain reach, but do so with robotic assistance. In particular, MIT-MANUS (Aisen et al., 1997), the mirror-image motion enabler robot (Burgar et al., 2000), the ARM-guide system (Reinkensmeyer et al., 2004), and the Bi-Manu-Track (Hesse et al., 2003) are conventional robot systems assisting the movements of the affected limb. Other recent developments include balancing assistance provided by the robot with active movement by the patient, e.g. (Kahn et al., 2004), and EMG triggered robots (Dipietro et al., 2005). Still others provide robots that focus on hand retraining (L. Dovat, O. Lambercy, R. Gassert, T. Maeder, T Milner, C. L. Teo, E. Burdet. HandCARE: a Cable-Actuated REhabilitation system to train hand function after stroke. IEEE Transaction on Neural Systems and Rehabilitation Engineering, 16(6): 582-591, 2008; O. Lambercy, L. Dovat, R. Gassert, E. Burdet, C. L. Teo, T. Milner. A haptic knob for rehabilitation of hand function. IEEE Transaction on Neural Systems and Rehabilitation Engineering, 15(3):356-366, 2007). These systems have been shown to be effective to some extent (Krebs et al., 1999a; Krebs et al., 1999b; Lum et al., 2002), and can be used with patients that have no or little residual movement capabilities. However, they are mostly limited to large research and clinical centers because they are expensive, complex to maintain, and require supervision and/or assistance to use. Importantly, these systems provide motor learning on the robot and not to everyday tasks. Outside the clinical setting, there is no robotic assistance available. Therefore, the effectiveness of conventional robots is limited. Other systems provide balancing assistance from a robot in conjunction with active movement by the patient. These solutions suffer from their expense, complexity and the need for well-trained supervision. These robotic systems may offer benefits adjunctive to motor learning, just as a therapist uses passive and active movement to enhance flexibility and strength of the peripheral structures of a limb. However, these systems do not address the need for active motor learning in the rehabilitative process through adaptive training on a plurality of functional tasks involving reach, grasping and manipulation.

Virtual reality (VR) systems are also known and allow users to practice reaching movements. Virtual reality (VR) systems have the advantages of lower price, 3D interactions, increased safety, and can easily embed motivation principles from computer games. VR system designed to enhance reaching movements in patients with stroke have been tested in small pilot studies (Merians et al., 2002; Piron et al., 2004; Stewart et al., 2007; Subramanian et al., 2007). However, VR systems require 3-D goggles or projection screens to create the illusion of a 3-D virtual world. Users of VR systems also require an adaptation phase in order to mentally map one's actions onto the virtual world. Simple VR, which is without the use of a robot, typically does not allow natural movement. For instance if reaching to a target in a VR system, the patient can inadvertently move their hand through the target or cross the target at high velocity, since there is no physical object or constraint. Therefore, there is difficulty in transferring motor learning in a VR environment to a real world environment with physical objects. This adaptation may especially be difficult for older stroke victims to overcome and some may not be able to perceive the virtual world without discomfort. Therefore, there still exists a need for effective systems and techniques to rehabilitate patients with neurological disorders such as strokes.

SUMMARY OF THE INVENTION

The present invention provides a method to measure voluntary paretic arm use, non-use and function in a quantifiable and repeatable manner for arm and hand function. Arm use is determined by free choice and is measured by instructing subjects to reach for targets on a two-dimensional workspace using the arm of their choice (free choice). Arm function is determined by forcing the use of an affected hand and measuring the performance on tasks. Arm non-use is measured by contrasting the probability of reach in a forced use sequence to the probability of using the arm in a free choice sequence. In other words, non-use is determined by comparing what a user can do with the affected arm (function) to what the user actually does (use) on the same tasks. The above-described method and system to measure paretic (impaired) arm use and non-use is simple to administer and requires minimal training of the participant and test administrator. The measurements are repeatable and provide reliable results.

The present invention is also suitable for use in rehabilitation of patients with motor impairment of an upper extremity resulting from stroke. The present invention provides a significant contribution to the field of stroke rehabilitation by addressing the need for a device that will deliver intensive task-oriented practice to patients at a relatively low cost with only minimal supervision by a rehabilitation therapist.

Furthermore, the present invention provides repetitive task practice with real-world challenges, and presents functional tasks automatically. A plurality of tasks are included and are controlled by an adaptive performance-based task controller that varies a plurality of parameters optimized for each patient. Adaptive training is understood as a computer processor determining the schedule of tasks to perform without relying primarily on user input. The limb rehabilitation system adapts the tasks to be performed to the patient, such that every patient can perform the task he or she is capable of, while continually being challenged and optimally stimulated by a variety of tasks. A critical means to improve functional outcomes in patients with stroke-related disability is to increase dramatically the amount of task practice, while maintaining overall costs at a reasonable level. One possible method to increase practice time in a cost-effective manner is to supplement the patient's one-to-one interaction with a physical therapist with sessions on an automated task practice system. In one embodiment of the present invention, a limb rehabilitation system is designed specifically to enhance the functional outcomes of patients with post-acute stroke who have deficits in motor tasks that require reaching and manipulation. The system can dramatically increase practice time, accurately monitor a patient's performance, and present a variety of challenging tasks adaptively to significantly improve the functional outcomes cost-effectively. The above and other objects of the present invention are achieved by a rehabilitation system in accordance with embodiments of the present invention and methods for using thereof.

Accordingly, one embodiment of the invention is a method for measuring an upper limb reaching capability of a user with an impaired limb. Each upper limb is placed at a default position on a horizontal surface. A target is displayed from among a plurality of targets on the horizontal surface. One of the limbs reaches for the target. Limb choice, position information and elapsed time are sensed and recorded. The reaching limb is retracted to the default position. The displaying step through the retracting step are repeated for each of the plurality of targets, wherein each of the plurality of targets is spaced apart.

Furthermore, free-choice is provided in the reaching limb for the plurality of targets. Alternatively, only the impaired limb is used for the reaching of the plurality of targets. A successful trial is determined when the reaching limb reaches the target within a pre-determined time. An amount of reach and an amount of non-use is calculated based on the limb choice, the position information and the elapsed time. A set of challenging reaching targets is determined based on the amount of use and the amount of non-use. A challenging target is displayed from the set of challenging reaching targets. Then, the impaired limb reaches for the challenging target. Position information and elapsed time of the impaired limb reaching is sensed and recorded. The impaired limb is retracted to the default position. The challenging target displaying step through the retracting step are repeated for each of the set of challenging targets. The targets are displayed by rising from below the horizontal surface, light-emitting diodes or a touchscreen. Each of the targets includes a touch sensor. The limb not reaching for the target remains in place at the default position.

In another embodiment of the present invention, a system for measuring an upper limb reaching capability of a user with an impaired limb is provided. The system includes a horizontal surface including a default position. Sensors for detecting limb choice, position information and elapsed time are provided. A target display device is provided to sequentially display a plurality of spaced apart targets on the horizontal surface. A controller is connected to the targeting device and the sensors. The controller calculates an amount of reach and an amount of non-use based on the detected limb choice, the position information and the elapsed time.

Furthermore, the targets are displayed by rising from below the horizontal surface, light-emitting diodes or a touchscreen. Each of the targets is formed of a plurality of nested targets. The sensors detect reaction time and movement time. The target display device further includes a plurality of light-emitting diodes and corresponding switches provided on the surface. The system includes a display device and an audio device providing instructions and feedback to the user. The controller determines a set of challenging reaching targets based on the amount of use and the amount of non-use.

In yet another embodiment, an upper limb re-training device is provided. A plurality of handheld objects are provided. An object manipulator is removably docked to one of the plurality of objects. Force, torque and position sensors are provided. A task controller is connected to the sensors and the object manipulator and the task controller determines a task schedule and task difficulty to control the object manipulator to position the object and to simulate the weight of the object based on previous performance, user data and operator input.

Furthermore, the object manipulator positions the object with at least four degrees of freedom. Each object includes an object plate and the object manipulator includes a docking plate docked with the object plate of one of the plurality of objects. The object manipulator further includes a pneumatic valve or electromagnetic system to dock and undock the docking plate to the object plate. The objects are selected from the group consisting of a jar, a bottle, a switch, keys, a doorbell, a doorknob, a faucet, a wheel, a screwdriver, a cylinder, a button, a handle, a utensil, pen and a gear shifter.

Other features and advantages of the invention will be apparent from the following detailed description, taken in conjunction with the accompanying drawings which illustrate, by way of example, various features of embodiments of the invention.

DETAILED DESCRIPTION OF THE INVENTION

To further illustrate the present invention, a more detailed discussion of the various possible embodiments of the present invention is provided below. It will be understood that these specific details are for the purpose of illustration only and are not to be construed as limiting in any way.

Figure 1:
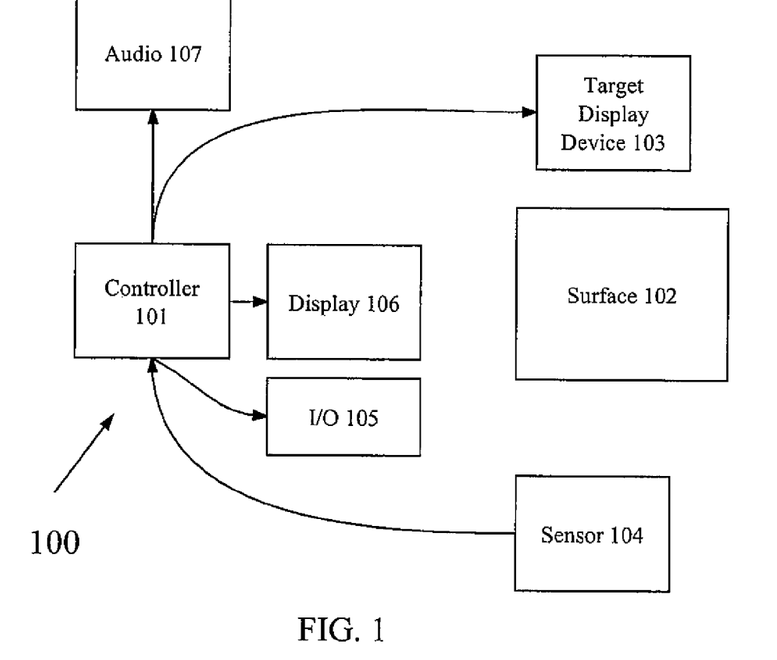
FIG. 1 is a block diagram of one embodiment of the upper limb reaching capability and re-training system of the invention.

FIG. 1 illustrates an arm use and non-use measurement system 100. In one embodiment, a controller 101, two-dimensional surface 102, target display device 103 and position sensor 104 are provided. The target display device 103 is for example, an overhead light projector. A user is seated next to the two-dimensional surface 102, such as a table, so as to be able to reach across the table with either hand. The controller 101 is connected to the target display device 103, the position sensors 104, an input device 105, as well as a display 106 and audio device 107 to provide user feedback. The controller 101 includes a storage device (not shown) that stores the measurement control program and the sensor data. The controller 101 also calculates the arm use and non-use from the position data collected.

Figure 2:
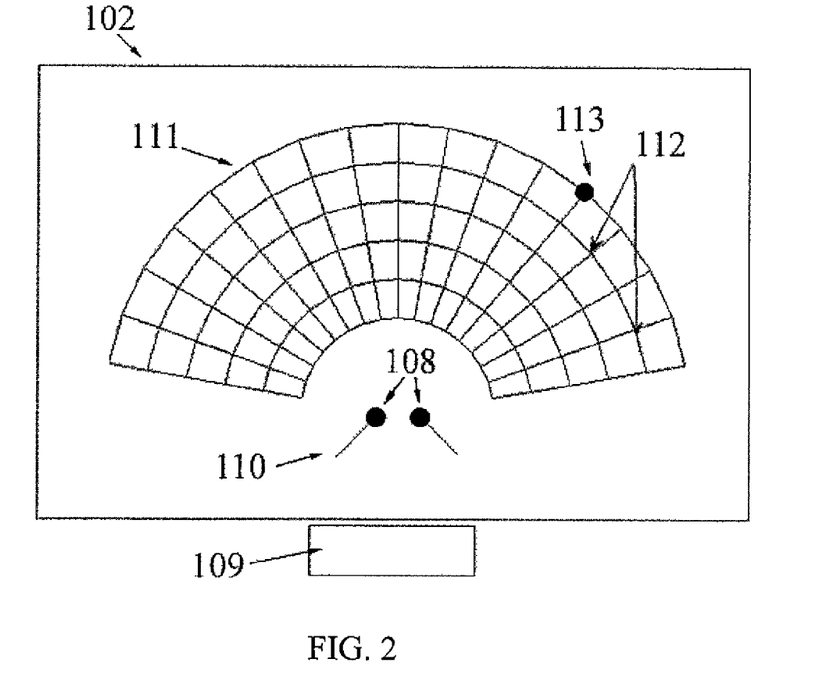
FIG. 2 is a plan view of one embodiment of the upper limb reaching capability and re-training system of the invention.

The top of the surface 102 is marked with a pair of predetermined default positions 108, as shown in FIG. 2. The user 109 begins by resting each hand at the default position 108 in front of where the user 109 is seated. Arm guides 110 are marked on the surface 102 to indicate the default position of the arms. The arm guides 110 may form a 45° angle with respect to an edge of the surface 102. The user 109 is seated comfortably in front of the surface 102 and may preferably be held in place by a restraint system such as straps or a chest belt such that a user 109 cannot move their torso or upper body to compensate for a paretic arm. Alternatively, user 109 may lean forward on a side edge of surface 102 against a bumper that restricts chest movement without impeding arm reach. The target display device 103 provides a plurality of illuminated targets on the surface 102 for a user to reach for. Of course, the targets should be within a radius of a user's arm length when seated.

In one embodiment, a set of 100 target positions 112 are equally distributed at every 10° between 10° to 170°, and every 4 cm between 10 cm to 30 cm, without the right-most and left-most targets. Target grid 111 provides intersecting lines representing the points where the target display device 103 will display a lighted target. The user does not see the lines of the target grid 111, but instead will just see one lighted target at a time. For example, a target 113 being a circle of white light having a radius of about 2 cm in diameter will appear randomly during a measurement sequence for a user to reach. In one embodiment, 100 targets are available to be displayed on the surface 102 by the target display device 103. Each target will appear twice randomly for a user to reach at, for a total number of 200 targets. The number of targets to be tested may vary with each user 109, time available or other factors. A light may also be provided at the default position 108 to direct the hand position of the user 109. Switches or buttons may also be placed on the surface 102 and illuminated to indicate the target 113. The user can place pressure on the lighted switch to indicate successful reaching.

Sensors 104 track the motion and position of a user's arm reach. In one embodiment, a miniaturized DC magnetic tracking system is used. For example, a Mini-Bird model 500 sensor (manufactured by Ascension Technology Corporation), is a small (5 mm) magnetic sensor that is easily attached to a hand or a finger to track the reaching movements of the arm. The sensors are lightweight and are attached to a long, thin cables such that movement of the arm is not affected by the use the sensors. The sensor cables can be taped to the user's upper extremities and are adjustable to allow a comfortable, fully extended reach. The magnetic sensors provide six degrees of freedom, translating into an unlimited range of motion and three-dimensional output data. The sensors 104 are capable of providing position and orientation measurements and can, for example, capture position data at approximately 40 Hz. The present invention is not limited to a magnetic tracking system as other motion tracker sensor systems may be utilized, as long as arm and hand movements in the reaching task are not significantly affected by the sensors. The sensor system records limb choice, position information and the time elapsed for a user to move from the default position to the target. Within the elapsed time, reaction times and movement times are recorded. Reaction time is defined as the difference in time between when the target 113 is displayed to the movement of the limb from the default position 108, and movement time is defined as the difference in time between when the limb moves from the default position 108 to reaching the target 113.

In another embodiment for a two-dimensional reaching task, the targets for reaching are LED lights embedded in the surface 102 along with corresponding switches or buttons for a user 109 to activate to record movement time. A switch or button is also provided at the default position 108 for recording reaction time and to ensure compliance with the measurement sequence. The surface 102 can alternatively be formed as a capacitive touchscreen display where a user may touch the display directly to accomplish the reaching task. The display itself provides the lighted target, functions as the position sensor, and also provides instructions, user feedback and other display prompts.

In yet another embodiment for a two-dimensional reaching and grasping task, a plurality of physical targets are provided in corresponding holes in the surface 102 and are raised up above the surface 102 to indicate an active target for a user to reach for and grasp. These pop-up targets are physical objects having force and/or torque sensors that detect user contact and which scores a successful trial when the user applies a pre-determined amount of grasp force on the risen target. Alternatively, the targets may incorporate touch sensors to detect contact. A pop-up target may be a nested target that includes a plurality of targets within the outermost target for grasping. For example, each pop-up target is made of one or several Matryoshka doll-type nested targets that need to be grasped. An inner cylinder of the nested target with a smaller cylinder for finer hand movements, such as pinching. The target to grasp is alternatively chosen from a plurality of everyday objects such as a cylinder, button, switch, bottles, jar, faucet, hand tool, gear shifter, telephone, etc. Any handheld or graspable object able to rise up from below the surface 102 for a user to grasp can be used in the arm measurement and training process. This embodiment has the additional benefit of measuring arm use and non-use for specific objects and provides physical, feedback to the user.

The arm use and non-use measurement process begins by a user sitting down in the seat and appropriately attaching the sensors and restraint system. Then, the user 109 is instructed by an operator or the display 106 and/or audio 107 to place their hands at the default positions 108. The measurement of arm use and non-use requires testing under a free-choice sequence and forced sequence.

If the free-choice sequence is selected first to be measured, the user 109 is instructed to reach for each successively displayed target 113 from the default position 108 with their choice of hand as quickly and accurately as possible, and to hold their fingers within the boundaries of the target 113 until the target 113 disappears. When the user 109 chooses an arm to reach and moves away from the default position 108, the light at position 108 disappears. During this time, the off hand is to remain at the default position 108. Then, the user 109 is to retract the reaching hand to the default position 108 for the next target. A successful trial is recorded when the target is reached within a pre-determined time period, such as 1.2 seconds. The pre-determined time is not limited to 1.2 second and can be varied as necessary. If a user 109 is unable to reach the target before the pre-determined time, the target 113 will disappear and the light at the position 108 will appear. An audible feedback and/or display is provided after each trial to indicate success and failure. The display 106 can also display to the user 109 the real-time results of the measurement sequence and may present the number of successful trials out of the last ten trails. A scoring system may also be implemented and displayed to make the process more game-like and interesting to the user. In the free-choice sequence, user 109 is instructed to maximize the number of successful trails and reminded that the choice of arm should be made accordingly. Furthermore, the user is instructed that dragging of the arm along the surface 102 should be avoided.

In the forced-use sequence, user 109 is instructed to reach each successively displayed target 113 using only the impaired paretic arm as quickly and accurately as possible. The conditions for successful and failed trails and feedback are the same as in the free-choice sequence. Testing in the free choice and forced use sequences can be accomplished in about 15 minutes each. Once the free-choice sequence and forced-use sequence are performed, the controller 101 then performs analysis of the measurement data to provide the arm use and non-use values. The analysis generated provides a progress report to the user and rehabilitation therapist and also allows the generation of adaptive training schedules for impaired limb re-training.

The system of FIG. 1 can also be configured to in a training mode where a user 109 is presented challenging reaching targets for reaching using the paretic (impaired) limb. The challenging reaching targets presented in the training mode are chosen based on the results of the measurement sequence. In order to provide an optimal challenge, the target position and the pre-determined time for reach may be varied adaptively by the controller 101. The optimal challenge will be assessed by the percentage of successful trials of each target. For example, only targets that have been reached successfully within a range of probabilities (i.e. 70%) will be selected for presentation in a distance training mode. Alternatively, the pre-determined time can be varied to achieve a pre-determined probability of successful reach (i.e. 70%) in a time training mode. Audio or visual prompts may be displayed to indicate if a pre-determined time is shortened. The distance and time can also be combined in a mixed training mode. In the distance and mixed training modes, the targets chosen will expand as the user's performance improves.

In order to optimize re-training, the challenges presented are within the capabilities of the user and the user also receives motivating feedback. Because a user's performance will presumably improve over the course of rehabilitation, tasks that were initially challenging become less so with more practice. Thus, adapting the tasks to each patient continuously will improve motor learning. For example, after a training session, a display of the newly reached targets not reached previously is displayed to show progress and provide encouragement. Furthermore, during training, the time delay between target presentation is kept constant, such that the number of targets reached will increase as the speed of reaching increases. A display of the average time of reaching movement and the number of targets per minute is provided as feedback. The constant inter-trial interval has the additional advantage that the faster the targets are reached, the shorter the training session will be. This reward to users is an effective motivational technique to optimizing user performance. Over time, the targets selected in the training mode will move farther away from the default position. Moreover, the allowable time to reach each target can be reduced as the user improves performance.

A second order logistic regression model is used to model the data to determine the amount of reach and the amount of non-use. Described below is one of many available methods for calculating amount of use, non-use, and challenging targets. The models can be further extended for grasping and grasping with pop-up targets, as well as all of the above-described functional tasks (reaching, grasping, manipulation) to provide two-dimensional and three-dimensional use and function maps. The probability of reaching successfully with each target with the affected (i.e., impaired, paretic) arm is obtained using the following formula:

$$P(\text{success, handChoice=affectedArm}|\text{target}) = P(\text{success}|\text{handChoice=affectedArm, target})P(\text{handChoice=affectedArm}|\text{target})$$

where P(success|handChoice=affectedArm, target) represents the success probability of the selected affected arm to a given target and P(handChoice=affectedArm|target) represents the choice of arm use.

The Amount of Reach (AOR) is computed by integrating the volume beneath the probability surface for the affected arm use in stroke participants and the dominant arm of a control group of healthy subjects, that is AOR=P(handChoice=affectedArm), where $$P(handChoice = affectedArm) = \sum_{success}\sum_{target} P\binom{success, handChoice = }{affectedArm, target}$$

$$= \sum_{success}\sum_{target} P\binom{success, handChoice =}{affectedArm \mid target} P(target)$$

The control group dominant arm was used to compute the AOR. The AOR is a probability, defined by the equation:

$$P(\text{handChoice=affectedArm})+P(\text{handChoice=unaffectedArm})=1$$

Figure 3A:
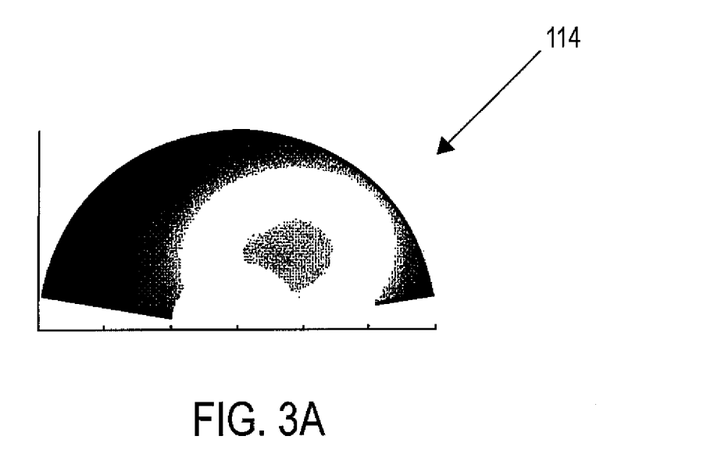
FIG. 3a shows an amount of reach map of one embodiment of the invention.

The maximum AOR is equal to 1 if the subject is able to reach targets over the whole 2D workspace. In practice, because of a slight preference in the contralateral space of the 2D workspace with the dominant arm, the AOU of the dominant arm is slightly greater than 0.5 in healthy subjects. The AOU can be much less than 0.5 in participants with stroke. FIG. 3a illustrates a two-dimensional, color coded AOR probability surface map 114. Dark areas show successful reach probabilities while lighter portions show areas of lower AOR probability on the surface 102.

Figure 3B:
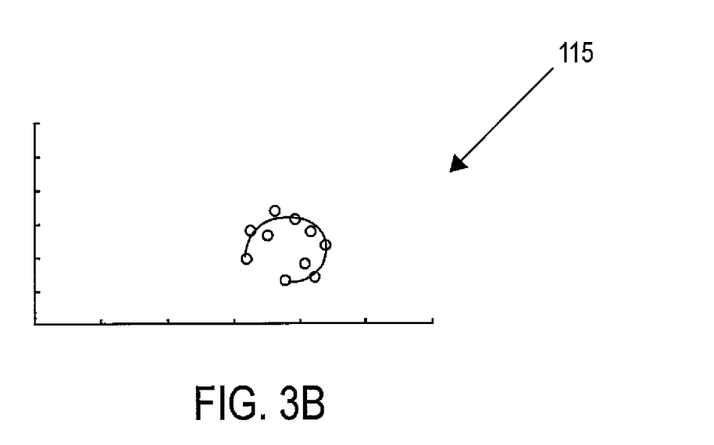
FIG. 3b shows a challenging target map of one embodiment of the invention.

FIG. 3b shows a surface map 115 of ten targets nearest to the line of 70% probability of reach success based on AOR map 114. In training mode, the 70% probability targets are selected as the set of challenging targets. If the user's reach performance with this set is poor, then it is possible that the challenge is too great. The next set of targets is then computed with an increase in allowable pre-determined movement time to ease the challenge to reach the 70% success rate. Similarly, if the reach performance is high, then the movement time can be decreased to provide a greater challenge.

The Amount of Non-Use (ANU) is calculated by comparing performance in a normalized forced-use sequence to that a free-choice sequence. Non-use for each target is calculated by multiplying the probability of reaching the targets in the forced condition by the average probability of reaching the target by healthy subjects (with same pre-stroke arm dominance), and then subtracting the probability of reaching the same target in the free choice condition. The amount of non-use for each target is thus given by:

$$ANU(\text{target}) = \left| P\binom{\text{success} \mid affectedArm,}{\text{target}} P_{healthy}\binom{handChoice =}{affectedArm \mid \text{target}} - P\binom{\text{success,}}{handChoice = affectedArm \mid \text{target}} \right|_+$$

where the function $|x|_+$ returns x if x>0 and 0 otherwise.

The complete ANU value is the sum of ANU (target) for all targets in the workspace and normalized to 1. In the above equation, the sum of the first term over the workspace, P(success|affectedArm, target) $P_{healthy}$ (handChoice=affectedArm|target), is called the maximum capability (MC). The second term is directly used in computation of AOR and measures free-choice use for each target. To compute the Maximum Capability for right hand dominant discordant patients, the probability of use $P_{healthy}$ (handChoice=rightArm|target) is reversed.

Figure 4:
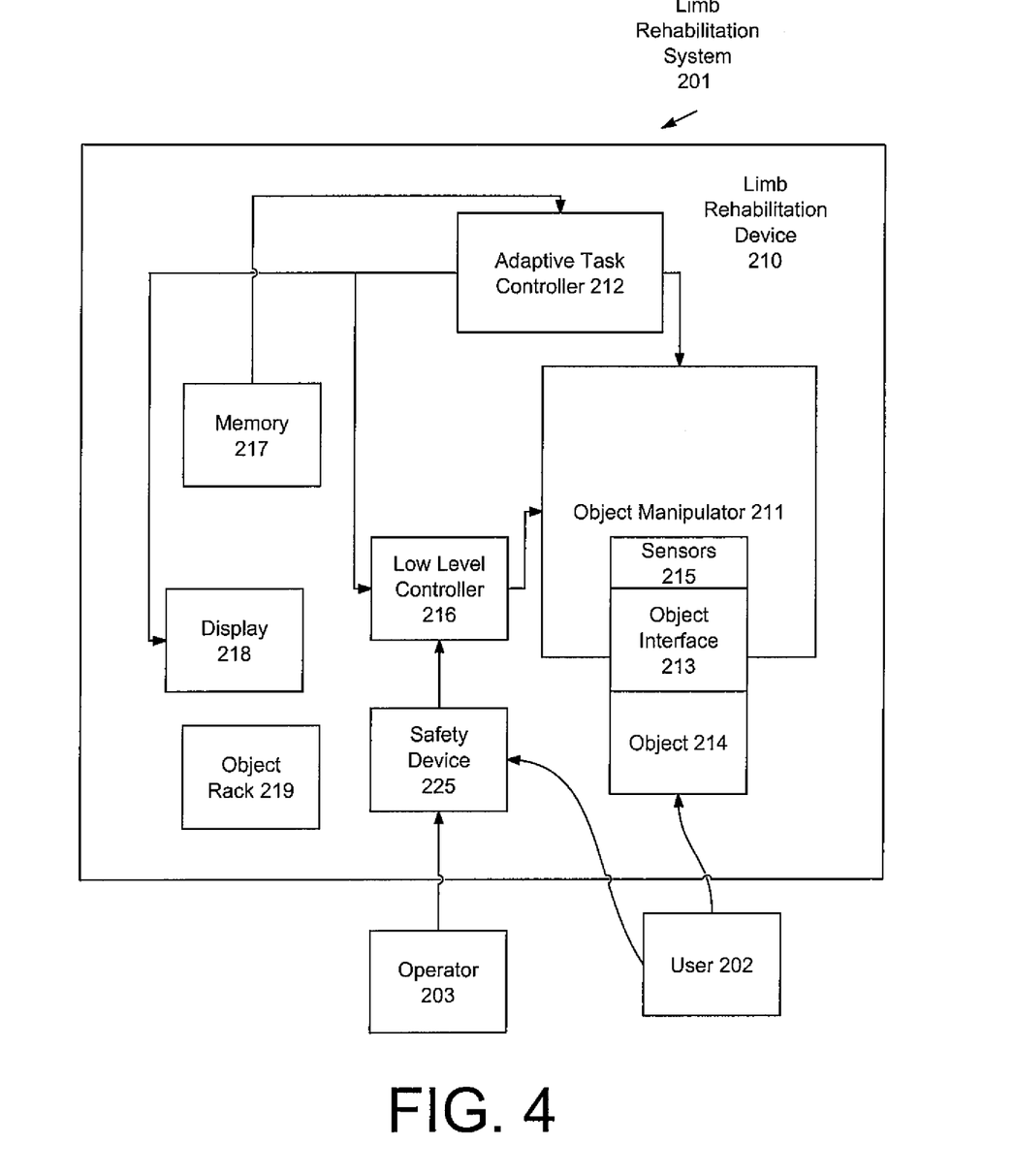
FIG. 4 is a block diagram of one embodiment of an upper limb rehabilitation system of the invention.

FIG. 4 is a block diagram of another embodiment of the limb rehabilitation system. The limb rehabilitation system 201 includes a limb rehabilitation device 210 that is a single integrated device or a set of discrete components functionally integrated. For example, the low level controller 216 and object manipulator 211 may be within the same device, but the adaptive task controller 212 and memory 217 may be provided in a separate computer connected to the object manipulator 211. FIG. 4 shows the components in a single device for ease of explanation.

The limb rehabilitation device 210 includes an adaptive task controller 212 for determining and setting the task control signals to an object manipulator 211. A display 218 and input/output device (not shown) provide feedback to an operator 203 and user 202. The operator 203 is, for example, a physical therapist that operates the device 210 without being required to manually input and initiate each task to be performed. A memory 217 is provided to store the software controlling the device 210 and also includes user data necessary to develop the task schedule.

The adaptive task controller 212 provides high-level control of all components of the rehabilitation device 210, while the low-level controller 216 outputs the control current necessary to operate the object manipulator 211 and the object interface 213. The object interface 213 acts as a tool changing system that changes the different tools or objects on the object rack 219. A plurality objects are available on the rack 219. The controller 212 adaptively chooses a task and difficulty based on a user's previous performance, operator input and user data for repetitive task practice of real-world challenges. For instance, the sensors 215 include a torque sensor and position sensor, and are discussed in detail below. A magnetic sensor tracking system may also be attached to a user's hand and arm to determine hand and shoulder position and orientation. Performance data is computed from the measured position and force/torque data. An object 214 from the object rack 219 is automatically selected by the controller 212 for any given task. The scheduler 212 generates a desired trajectory to simulate the dynamics of the task with the difficulty determined by the scheduler 212 as well. A set of challenging targets may be determined for the object manipulator in a manner analogous to that described for the system of FIG. 1.

The object manipulator 211 is, for example, a general purpose, modular robot such as an AMTEC Robotics robot having a 3 degree-of-freedom (DOF) wrist mounted on a 1-DOF linear actuator. Therefore, the object manipulator 211 is a 4-DOF robot. However, any robotic arm able to position its end-effector in three-dimensional space and at least three orientations and able to compensate for its own inertia and gravity may be used. This configuration allows an end-effector (object interface 213) to be positioned at different linear vertical positions and to allow rotation of the end-effector in almost any orientation. High torque can be generated to manipulate the objects on the object interface 213 with a small physical footprint by the robot. A smaller, less complicated object manipulator 211 also provides an increased margin for safety to the user 202. The functionality of the robot can be further extended with the addition of other linear and angular modules for increasing the range of motion. For example, two extra linear modules allow more complicated tasks including those requiring shoulder motions. A safety device 225 continuously monitors the status of the object manipulator 211 and the controllers in the system 201 and provides appropriate action to minimize any risk to the user 202.

Figure 5:
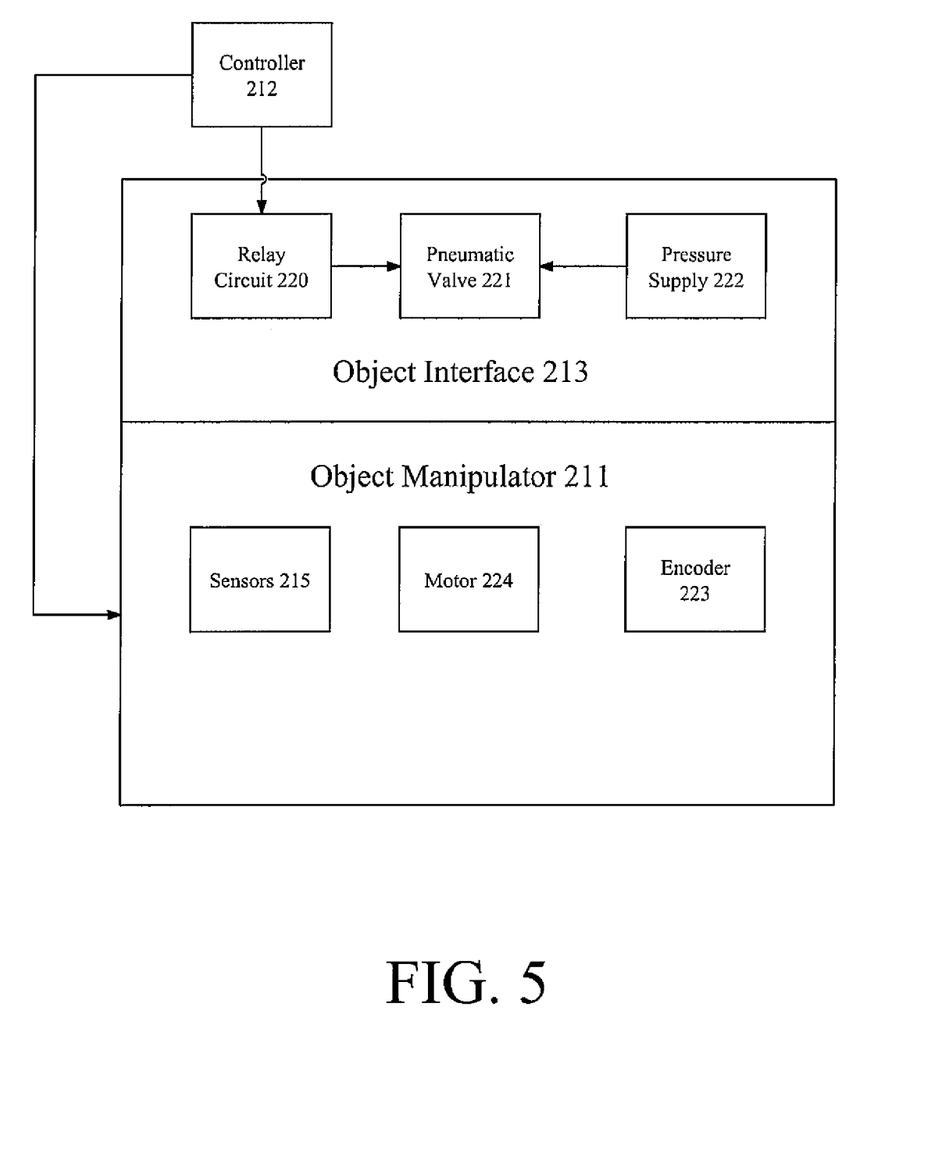
FIG. 5 is an block diagram of the object manipulator of the rehabilitation system of the invention.
Figure 6:
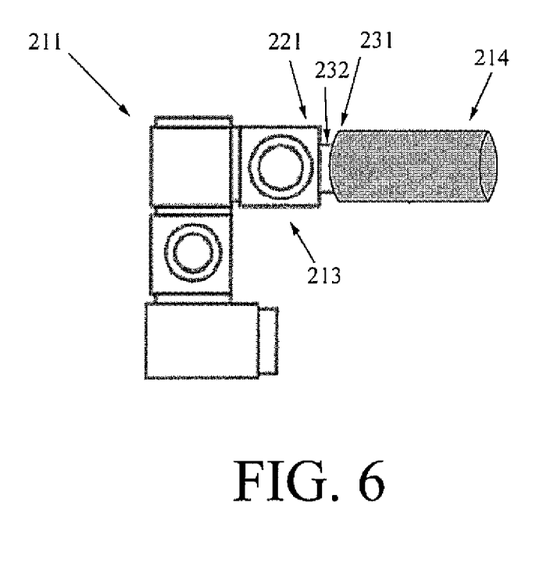
FIG. 6 is a side view of one embodiment of the object manipulator of the invention.
Figure 8:
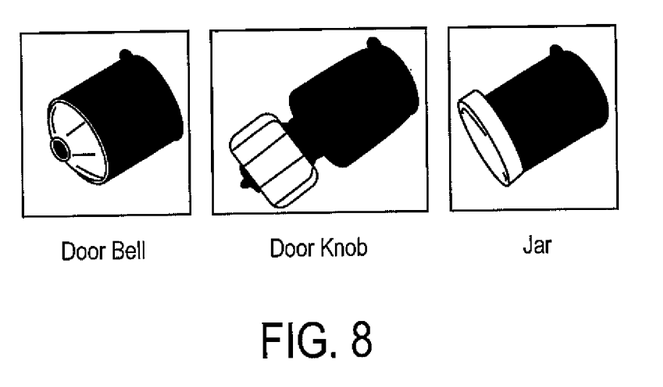
FIG. 8 is an illustrative example of the objects to be manipulated in one embodiment of the invention.

The object interface 213 is a multi-purpose end-effector tool mounted to the end of the object manipulator 211. The object interface 213 includes a 6-DOF force/torque (F/T) sensor to measure interaction forces between the user 202 and an attached object. Furthermore, encoders 223 in the object manipulator 211 provide position data of each joint. The object interface 213 connects to an object 214 that is a functional task tool, such as a doorknob. Other functional task tools available in the object rack 219 for a user to manipulate include, but are not limited to a screwdriver, jar, faucet, keys, bottles, gear shifter, telephone, etc. As seen in FIG. 6, the object interface 213 is equipped at its end with a docking plate 232 that connects to an object 214 via an object plate 231. Each of the objects 214 are attached at an end of an object plate 231. A pneumatic valve 221 ensures the locking and unlocking of the object 214 to the object interface 213 using the pressure supply 222 (FIG. 5). In particular, the pneumatic valve 221 is a 4/2-way pneumatic valve (V5 A-3341-BX1, MEAD Corporation), which is controlled via RS-232 serial communication protocol to controller 212. To attach an object 214 to the object manipulator 211, the controller 212 transmits a command to relay circuit 220 so that the docking plate 232 of the object interface 213 docks and locks with the object plate 231 of the object 214. The object manipulator 211 is then repositioned to present the object 214 to the user 202 at a pre-determined position for reaching and grasping tasks. FIG. 8 illustrates everyday handheld objects attached at one end to an object plate. Furthermore, an electromagnetic docking system may be utilized instead of a pneumatic valve. The object manipulator 211 may further contain a plurality of objects 214 at the object interface 213 on a rotary plate, where the desired object is presented by appropriate rotation of the plate.

Figure 7:
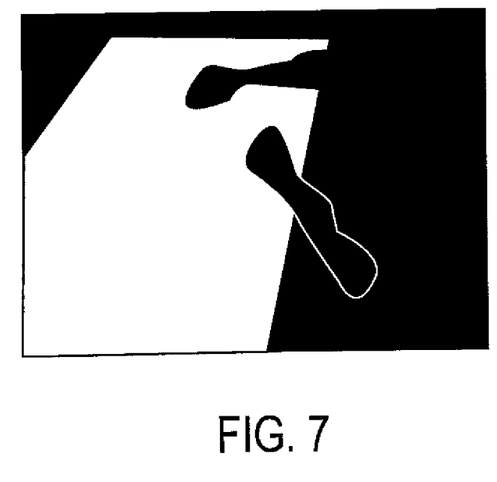
FIG. 7 is an illustrative example of a restraint system of one embodiment of the invention.

A user 202 is seated facing the object manipulator 211 and object 214. As discussed above, a restraint system can be provided to reduce possible compensatory torso movements (FIG. 7). A surface such as a table is provided for the user 202 to rest their hands. Different objects presented to the user allow for practice of a variety of reaching and grasping tasks. Once the object 214 is presented to the user 202, magnetic brakes built into the object manipulator 211 engage on the other 3-DOF to prevent movement. Allowing just a single DOF simplifies kinematics such that the object manipulator 211 never falls into the wrist-singular posture, which can occur in PUMA-like manipulators. The object's weight is simulated by the object manipulator 211 by gravity and inertial compensation. The object manipulator's weight and inertial force are compensated such that when a user interacts with the object 214, the weight and inertia of the object manipulator 211 will not be felt by the user.

Safety device 225 limits the maximum torque output and velocity of the linear and rotational motors 224. Failure of the position and force sensors 215, controller 212 and power are continually monitored. If a failure is detected, the safety device 225 automatically engages the magnetic brakes in every degree of freedom. Furthermore, safety device 225 includes an emergency stop button for the operator 203 and the user 202. The user 202 preferably holds the emergency stop button in the non-impaired hand. Furthermore, the user is not strapped to the object manipulator 211 and is therefore able to more easily move away from object manipulator 211 if malfunction occurs. In addition, for the sake of simplicity and safety, the functional tasks performed require user movement around only a single-degree of freedom. Many functional tasks in daily living, such as turning a key or door knob, steering, opening a jar, wrist supination/pronation, etc. require only a single rotary degree of freedom.

For example, the task to perform may be, for instance, to grab a bottle at 30 cm in front of the user and move it to a predetermined position. For this trial, position could be adapted based on performance. First, the object manipulator 211 will orient the object interface 213 and adjust the forces applied in the interface 213 to simulate the weight of a bottle, as if the bottle is not held by the object manipulator 211. Each task is defined by parameters such as object position, orientation in 3D space, distance of movement, speed, torque and force compensation to be applied, etc. A display 218 will then instruct the user to reach and lift the bottle. For a doorknob turning task, a trial is a success if the user turns the doorknob at or beyond a pre-determined target angle. For a jar opening/closing task, the trial is a success if the subject closes the jar lid at or beyond a pre-determined angle. For the doorbell pushing task, the trial is a success if the pushing force is higher than a threshold force.

Because a patient's performance will presumably improve over the course of rehabilitation, tasks that were initially challenging become less so with more practice. Thus, adapting the tasks to each patient continuously will improve motor learning. The adaptive performance based task scheduling and adaptive difficulty allows each user to perform the task within their capabilities while being constantly optimally challenged. As the user's performance improves, heuristics may be used to modify adaptively the position of the end-effector and the force needed to move or rotate the object. Optimal challenge will be assessed by the movement times and by the successful completion of tasks. If, for instance, the controller 212 determines that the user cannot reach a bottle 30 cm away, then the bottle will be brought incrementally closer. Inversely, if the user can repeatedly perform the task rapidly with no errors, the bottle will be presented farther away or in a different portion of the workspace. Difficulty can be adjusted using a variety, of parameters, such as the time, force required, simulated weight and distance. Furthermore, the rehabilitation and training is presented as a game to the user to increase motivation. The invention is easy to operate and comprehend and practical to regaining function in everyday life.

The desired trajectory of a task and difficulty is sent as a control signal from the task controller 212 to the object manipulator 211 and is modeled as a locally weighted regression problem with receptive field weighted regression (RFWR). A Karnopp model is used to simulate the dynamics of passive tools with a haptic interface. The following models allow a desired feel or difficulty of the task tools to be adjustable.

Given training data point x, the predicted regression value y is:

$$y = \frac{\sum_{k=1}^{K} w_k y_k}{\sum_{k=1}^{K} w_k} \quad (1)$$

$$y_k = x^T b + b_{0,k} = \vec{x}^T \beta_k,$$

$$\vec{x} = (x^T, 1)^T$$

where $y_k$ is the individual prediction from each local linear model (each has a receptive field), $\beta_k$ is the local linear model parameter, and the weights $w_k$ corresponds to the activation strength of each receptive field. The weights are determined from the size and shape of each receptive field, characterized by a Gaussian kernel function, as commonly used in RFWR:

$$w_k = \exp(-\tfrac{1}{2}(x_{dep}-c_k)^T D_k (x_{dep}-c_k)) \quad (2)$$

where $D_k$ is a positive definite distance matrix, $x_{dep}$ is the state variable for the dependency of local models (e.g., position), and $c_k$ is the center of $k^{th}$ linear model in the dimension of $x_{dep}$. The state variable $x_{dep}$ is made of one or several elements of the input vector x in (1). For example, if $x_{dep}$ is an angle, then the local model $y_k$ for RFWR is created or pruned in terms of angle space. While learning with RFWR, the parameter $\beta_k$ is updated for each local linear model, and the distance matrix $D_k$ is updated to determine the shape and size of the receptive field. For each 1-DOF task, y is the torque output of the dynamics model for the current state x (e.g., angle, velocity, and acceleration). Each $y_k$ in (1) is formulated by a modified Karnopp friction model function, described below.

The linear equation for the dynamics of a 1-DOF rotary tool (e.g., doorknob) can be expressed by:

$$\tau_{measure} = \tau_{inertia} + \tau_{friction} + \tau_{misc} + \varepsilon = I_{tool} \times acc + C_p \mathrm{sgn}(vel_p) + b_p vel_p + C_n \mathrm{sgn}(vel_n) + b_n vel_n + \tau_{misc} + \varepsilon \quad (3)$$

where $I_{tool}$ is the inertia of the tool, $\tau_{measured}$ is the measured force, $C_p$ and $C_n$ are the positive and negative values of the dynamic friction, $b_p$ and $b_n$ are the positive and negative values of the viscous friction, acc is the angular acceleration, $vel_p$ is the positive value of the angular velocity (if the velocity is not positive, it is zero), $vel_n$ is the negative values of the angular velocity (if the velocity is not negative, it is zero), $\varepsilon$ is a noise factor, and $\tau_{misc}$ is other physical properties, such as stiffness in case of a doorknob. In (3), by adding $\tau_{misc}$, the modified Karnopp model is generalized to any passive 1-DOF rotary tools. The vector form corresponding to (3) to be used in (1) is:

$$\tau_{measured} - \tau_{inertia} = [\mathrm{sgn}(vel_p)\ vel_p\ \mathrm{sgn}(vel_n)\ vel_n] \begin{bmatrix} C_p \\ b_p \\ C_n \\ b_n \end{bmatrix} + \quad (4)$$

$$\tau_{misc} + \varepsilon$$
$$= x\beta' + \tau_{misc} + \varepsilon$$
$$= x\beta + \varepsilon$$

where $\tau_{misc}$ is assumed to be a linear function of x, the state vector, and $\beta$ is a parameter vector that can be formulated as in (1). If $\tau_{misc}$ is assumed only to be due to stiffness (e.g., a doorknob), then the state vector and parameter vector will be:

$$x = [\mathrm{sgn}(vel_p)\ vel_p\ \mathrm{sgn}(vel_n)\ vel_n\ ang_p\ ang_n]$$

$$\beta = [C_p\ b_p\ C_n\ b_n\ K_p\ K_n]^T \quad (5)$$

where $K_p$ and $K_n$ are the stiffness values for positive and negative velocities, and $ang_p$ and $ang_n$ are angles. To adjust the difficulty of a functional task, $\beta$ is multiplied by a difficulty value Diff or, if Diff is assumed to be a vector to multiply $\beta$ element-wise by Diff. Inertia is excluded from the parameter vector because inertia is assumed to not be state-dependent. Other parameters ($D_p$, $D_n$, and v) are obtained empirically.

After the model of (1), which uses with the local linear model of (4), is learned from the training data, the dynamics model for the functional task tsk, and difficulty Diff can be assumed to be:

$$y(tsk, Diff) = \frac{\sum_{k=1}^{K} w_k y_k}{\sum_{k=1}^{K} w_k} \quad (6)$$

$$y_k = x^T b_k + b_{0,k} = \vec{x}^T \beta_k Diff$$

$$\vec{x} = (x^T, 1)^T$$

where it is assumed that $\beta$ of (4) or (5) (the modified Karnopp model) is equal to each $\beta_k$. Then, by inserting (6) into (4), the desired trajectory can be derived:

$$\tau_{measured} - \tau_{inertia} = \tau_{measured} - I_{tool} acc = y(tsk, Diff) \quad (7)$$

$$acc_d = acc = \frac{\tau_{measured} - y(tsk, Diff)}{I_{tool}}$$

$$vel_d = vel + \frac{\tau_{measured} - y(tsk, Diff)}{I_{tool}} \Delta t$$

$$ang_d = vel_d \Delta t$$

where (ang, acc, vel) is a current state vector, ($ang_d$, $vel_d$, $acc_d$) is a desired state vector, and $\Delta t$ is a sampling time. The current state vector is measured by the encoder 223 at each time step. Other models may be used to model tasks. For example, tasks may be modeled using a combination of inertia, damping and friction with simple dynamics models.

The following are examples of exemplary tasks. In the simulation of reaching for a doorbell and ringing the bell, the ring is modeled by a cylinder of the manipulator end-effector in a horizontal position, such that the bottom of the cylinder is facing the subject. Parameters of the task that control the difficulty of the tasks are, the position of the bell in 3D space, and the amount of force needed to ring the bell. A bell will ring when sufficient amount of force is applied.

In a door opening simulation, the task is made of three-sub tasks that can be trained independently or in combination and that aim at simulating the user reaching for a knob, turning the knob to the left or right; and either pushing or pulling a door. The manipulator end-effector is positioned horizontally such that the user must grasp the end effector in a pad-opposition manner. Parameters that control the difficulty of the tasks include the position of knob in 3D space, the amount of force needed to rotate the knob, and the direction of the required rotation. The knob may be modeled as a rotary spring.

In another simulation, an object is picked up, transported and released. This task consists of three sub-tasks that can be presented together or independently: The user 1) picks up an object (e.g., an empty or a full bottle); 2) transports the object to a pre-determined position on a surface in front of the user; 3) releases the object. The end-effector is positioned vertically such that the user must grasp the end-effector in a power grasp fashion. Task difficulty is controlled by the initial distance and position of the object, the transport distance, and by the weight of the object (adjusted by the controller).

Furthermore, the adaptive limb re-training systems described above can be extended to reliably quantify arm use and performance in patients with other neural conditions such as Parkinsons' disease, focal dystonia and even scapular pain. The present invention allows a user to practice reaching and grasping tasks without direct assistance from a robot. The object manipulator provides force compensation to simulate the weight and feel of real-life handheld objects to increase the effectiveness of task practice. The difficulty of the tasks are chosen and varied in real-time by the system based on performance to provide an optimal challenge for efficient motor learning. Detailed feedback is also provided to the user to encourage further progress.

In sum, the system 100 of FIG. 1 provides horizontal measurement, as well as reaching and grasping practice on a two-dimensional plane. The surface 102 is alternatively a vertical plane providing measurement, reaching, manipulation and grasping practice. Pop-up or lit-up targets provide physical targets for reaching and grasping practice on a two-dimensional plane. Next, the system 210 of FIG. 4 implements similar features in three-dimensional space to provide arm use, function and non-use measurement if the system is extended to include additional degrees of freedom. Each of the above-described systems may function in a training mode where an impaired limb undergoes repetitive task practice under conditions of adaptive difficulty by varying parameters of position, time, force, etc optimized for each individual. A plurality of everyday handheld or hand operated objects are available for reaching grasping task practice and are switched automatically according to the automatic task scheduler. Furthermore, a plurality of object manipulators are provided so that a plurality of objects are positioned and oriented as desired throughout three-dimensional space. Each of the objects is replaceable with other objects as determined by a task scheduler. Each of the above-described systems may be modified to provide arm use and non-use measurement in a forced use or free-choice condition so as to provide horizontal, vertical or three-dimensional measurement.

The particular embodiments of the invention described in this document should be considered illustrative, rather than restrictive. Modification to the described embodiments may be made without departing from the spirit of the invention as defined by the following claims and their equivalents

The invention claimed is:

1. A system for measuring an upper limb reaching capability of a user with an impaired limb, comprising:
   a horizontal surface including a default position;
   sensors for detecting limb choice, position information and elapsed time;
   a target display device displaying sequentially a plurality of spaced apart targets on the horizontal surface; and
   a controller operably connected to the target display device and the sensors,
   wherein the controller is configured to adaptively present the user with a series of targets to reach for based on the user's past performance, and to determine a measurement for the user's upper limb reaching capability based on a set of parameters comprising voluntary paretic limb use, non-use and limb function, and
   wherein the controller measures non-use of the limb by comparing the probability of reach in a forced use sequence to the probability of using the limb in a free choice sequence.

2. The system according to claim 1, wherein the targets are displayed by rising from below the horizontal surface, light-emitting diodes or a touch screen.

3. The system according to claim 1, wherein each of the targets is formed of a plurality of nested targets.

4. The system according to claim 1, wherein the target display device includes a plurality of light-emitting diodes and corresponding switches provided on the surface.

5. The system according to claim 1, wherein the sensors detect reaction time and movement time.

6. The system according to claim 1, further comprising a display device and an audio device providing instructions and feedback.

7. The system according to claim 1, wherein the controller is further configured to determine a set of challenging reaching targets based on the amount of use and the amount of non-use.

* * * * *